US008187882B2

(12) United States Patent
Burns et al.

(10) Patent No.: US 8,187,882 B2
(45) Date of Patent: *May 29, 2012

(54) MULTIPLE SHOOT PROLIFERATION AND REGENERATION SYSTEM FOR PLANTS

(75) Inventors: John Austin Burns, Wildwood, MO (US); Lori A Smith, Lake Mills, WI (US); Dannette C Ward, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 759 days.

This patent is subject to a terminal disclaimer.

(21) Appl. No.: 11/103,682

(22) Filed: Apr. 12, 2005

(65) Prior Publication Data

US 2005/0183160 A1 Aug. 18, 2005

Related U.S. Application Data

(62) Division of application No. 09/683,548, filed on Jan. 16, 2002, now Pat. No. 6,900,057.

(60) Provisional application No. 60/261,904, filed on Jan. 16, 2001.

(51) Int. Cl.
*C12N 12/29* (2006.01)
*C12N 15/82* (2006.01)

(52) U.S. Cl. .................... 435/430.1; 435/468; 435/430; 435/415; 435/426; 435/427; 435/431; 800/278

(58) Field of Classification Search .................. 800/294, 800/314, 312, 268, 278; 435/468, 430, 430.1
See application file for complete search history.

(56) References Cited

U.S. PATENT DOCUMENTS

| | | | | |
|---|---|---|---|---|
| 5,004,863 | A * | 4/1991 | Umbeck | 800/314 |
| 5,164,310 | A | 11/1992 | Smith et al. | |
| 5,416,011 | A | 5/1995 | Hinchee et al. | 435/172.3 |
| 5,914,451 | A | 6/1999 | Martinell et al. | 800/300 |
| 5,959,179 | A | 9/1999 | Hinchee et al. | 800/298 |
| 5,998,207 | A | 12/1999 | Reichert et al. | 435/430 |
| 6,420,630 | B1 | 7/2002 | Wilson et al. | |
| 6,900,057 | B2 * | 5/2005 | Burns et al. | 435/430.1 |

OTHER PUBLICATIONS

Bajaj et al (1986, Indian Journal of Experimental Biology 24:581-583).*
George (1993, Plant Propagation by Tissue Culture, Exegetics Ltd, Great Britain, p. 469).*
Mohamed-Yasseen et al (1990, PGRSA Quarterly 18(4):203-210).*
Zilkah et al (1978, Planta 142:281-285).*
Agrawal et al., In vitro induction of multiple shoots and plant regeneration in cotton (*Gossypium hirsutum* L.), *Plant Cell Reports* 161:647-652 (1997).
Arteca, Manipulation of growth and photosynthetic processes, *Plant growth substances: principles and applications*, Chapman & Hall (New York), p. 247-248(1996).
Bajaj et al., Micropropagation and germplasm preservation of cotton (*Gossypium* spp.) through shoot tip and meristem culture, *Indian Journal of Experimental Biology* 24:581-583 (1986).
Bajaj, Micropropagation and conservation of germplasm of cotton, *Biotechnology in Agriculture and Forestry 42, Springer-Verlag* (New York), p. 60-67 (1998).
Bharati et al., Sodium-Dikegulac induced biochemiscal changes in seeds of a few crop species, *Environment & Ecology* 12:399-403 (1994).
Choudhury et al, Effect of dikegulac on biomass and alkaloid production in *Catharanthus roseus* (L) G. Don under in vitro condition, *Indian Journal of Experimental Biology* 37:594-598 (1999).
Choudhury et al., Effect of Dikegulac on Growth and Alkaloid Production in *Catharanthyus roseus* (L.) G. Don. (Pink flowered), *J. Plant Biol.* 41:149-154 (1998).
deSilva et al., Chemical Pinching of Azalea with Dikegulac, *HortScience* 11(6):569-570 (1976).
George, Compounds which can arrest apical growth, *Plant Propagation by Tissue Culture, Exegetics Ltd.*, Great Britain, p. 469 (1993).
Gould et al., Regeneration of *Gossypium hirsutum* and G. barbadense from shoot apex tissues for transformation, *Plant Cell Reports* 10:12-16 (1991).
Gupta et al., In vitro proliferation of shoots and regeneration of cotton, *Plant Cell, Tissue and Organ Culture* 51:149-152 (1997).
Hemphill et al., Rapid in vitro plant regeneration of cotton (*Gossypium hirsutum* L. *Plant Cells Reprots, Springer-Verlag* 17:273-278 (1998).
Jackson et al., *Journal of Horticultural Science* 52:169-71 (1977).
Maity et al., Regulatory Actions of $GA_3$, IAA and Sodium-Dikegulac on Detached Leaf Senescence of Two Ecologically Different Plant Species, *Environment & Ecology* 17:327-332 (1999).
McCabe et al., Transformation fo elite cotton cultivars via particle bombardment of meristems, *Bio/Technology* 11:596-598 (1993).
Mohamed-Yasseen et al., *PGRSA Quarterly* 18(4):203-210 (1990).
Mone et al., Multiple shoot induction and plant regeneration from embryonic axes of cotton, *Plant Cell, Tissue and Organ Culture* 54:131-136 (1998).
Purohit et al., Effects of dikegulac-sodium on negative geotropic response, endogenous tryptophan and IAA-oxidase activity in *Glycine max* roots, *Experientia* 37:148-149 (1981).
Saeet et al., A simple procedure of Gossypium meristem shoot tip culture, *Plant Cell, Tissue and Organ Culture* 51:201-207 (1997).
Sirois et al., Plant Growth Regulators and Leaf Characteristics of Soybean, *Proceedings of the Plant Growth Regulator Society of America*, Eighth Annual Meeting, pp. 107-113 (1981).
Snir, In vitro micropropagation of sweet cherry cultivars, *Proc. 5th Intl. Cong. Plant Tissue & Cell Culture: Plant Tissue Culture*, p. 735-736 (1982).
Ulian et al., Transformation of plants via the shoot apex, *In vitro Cellular and Developmental Biology* 21(9):951-954 (1988).
Zapata et al., Improvements in shoot apex regeneration of two fiber crops: cotton and kenaf, *Plant Cell Tissue and Organ Culture* 56:185-191 (1999).
Zapata et al., Transformation of a Texas cotton cultivar by using Agrobacterium and the shoot apex, *Theor. Appl. Genet.* 98:252-256 (1999).

(Continued)

*Primary Examiner* — Stuart F Baum
(74) *Attorney, Agent, or Firm* — SNR Denton US LLP; Thomas P. McBride Esq.

(57) ABSTRACT

Improved methods for the regeneration of transgenic plants using apical dominance inhibitors are disclosed. Use of dikegulac to induce multiple shoot formation in culture is particularly disclosed.

12 Claims, 2 Drawing Sheets

OTHER PUBLICATIONS

Zilkah et al., Cell cultures vs., whole plants for measuring phytotoxicity. I. The establishment and growth of callus and suspension cultures; definition of factors affecting toxicity on calli, *Plant & Cell Physiol. 18*:641-655 (1977).

Zilkah et al., Cell cultures vs. whole plants for measuring phytotoxicity. II. Correlations between phytotoxicity in seedlings and calli, *Plant & Cell Physiol. 18*:657-670 (1977).

Zilkah et al., Cell cultures vs. whole plants for measuring phytotoxicity. III. Correlations between phytotoxicities in cell suspension cultures, calli and seedlings, *Plant & Cell Physiol. 18*:815-820 (1977).

Zilkah et al., Differential inhibition by dikegulac of dividing and stationary cells in in vitro cultures, *Plants 142*:281-285 (1978).

Desfeux et al., "Female reproductive tissues are the primary target of agrobacterium-mediated transformation by the arabidopsis floral-dip method," *Plant Physiology*, 123:895-904, 2000.

Zhang et al., "Phenotypic variation in cotton (*gossypium hirsutum* L.) regenerated plants," *Current Sci.*, 81(8):1112-1115, 2001.

Zhang et al., "Recent progress in cotton biotechnology and genetic engineering in China," *Current Sci.*, 79(1):37-44, 2000.

* cited by examiner

MULTIPLE SHOOT PROLIFERATION AND REGENERATION SYSTEM FOR PLANTS

This application is a divisional application of U.S. application Ser. No. 09/683,548, filed Jan. 16, 2002, now U.S. Pat. No. 6,900,057, which claims priority to U.S. Provisional Patent Application No. 60/261,904, filed Jan. 16, 2001, both of which are herein incorporated by reference in their entirety.

BACKGROUND OF INVENTION

The invention relates to methods of plant regeneration. Specifically, methods utilizing media containing apical dominance inhibitors to induce multiple bud and shoot formation are disclosed. More specifically, methods for improving the efficiency of production of transgenic cotton and soybean plants are disclosed.

The expanding field of biotechnology provides the tools for scientists to introduce important traits into a variety of plant species. New technologies promote the production of commercially viable transgenic crops and have a significant economic impact on the agricultural industry. These advancements enable creation of new crop germplasm containing desirable novel traits. Such traits include improvements in the nutritional quality, insect resistance, disease resistance, and yield of many crops. Cotton is the leading fiber crop worldwide and holds significant agronomic influence in a number of markets. Accordingly, much effort is continually directed toward the genetic engineering of this agronomically important crop species.

Crop improvement is achieved with greater ease and rapidity when breeders are able to grow plant tissues in culture in such a way that whole plants, or portions thereof, can be rapidly produced from relatively high proportion of explants and from the most genotypically significant germplasm. The breeding and genetic engineering of cotton, however, has taken place at a relatively slow rate because of the absence of tissue culture methods capable of regenerating organized tissues, such as whole plants or shoots from cotton explants at a sufficiently high frequency and in a commercially timely manner from high-quality or commercial-quality germplasm.

Genetic engineering of plants is essentially a two-step process: transformation and regeneration. First, plant cells are transformed, thereby introducing a nucleic add sequence that is typically integrated into the genome of the host cell. Second, a sexually competent plant is regenerated from the transformed cells or tissues. In the most common method, nonembryogenic tissue is genetically transformed, then induced under suitable culture conditions to form somatic embryogenic calli. The embryos resulting therefrom may then be germinated to form plants. The transformation and regeneration processes preferably are complementary such that the successfully transformed tissues are capable of developing into competent whole plants.

Current systems are very time-consuming and laborious and a high frequency of plants that are recovered are not fertile. Meristem-based transformation systems are advantageous in that they are faster, but the plants are chimeras and it is difficult to identify germline transformants. If multiple shoots could be produced from the transformed meristem cells, then improved selection schemes could be utilized and nonchimeric transformed plants could be produced. Typically, cytokinins are used to produce a multiple shoot response in plants. However, in cotton, cytokinins only produce a few shoots in many cultivars or kill the explants entirely.

The present invention provides a method of culturing cotton and soybean that produces multiple shoots in culture and allows for the recovery of fertile plants. This allows for more efficient transformation and regeneration of cotton and soybean.

SUMMARY OF INVENTION

The methods disclosed in the present invention provide transformation and regeneration techniques to better meet the production needs of cotton and soybean breeders and growers. The invention allows more effective production of transgenic cotton germplasm, as well as improved efficiency in the regeneration of whole cotton plants. It is particularly useful in the case of recalcitrant elite varieties and extends the range of germplasm available for transformation. The method can also be used for soybeans and other dicotyledonous plants.

The invention involves the regeneration of a plant by providing an explant that includes a shoot apical meristem or primordia, inducing shoot formation by the use of an apical dominance inhibitor, and then rooting the shoot to produce a plant. In an embodiment, the plant is transgenic by the genetic transformation of the explant or the shoots that are formed.

In an embodiment of the invention, the apical dominance inhibitor is dikegulac.

The shoot culture medium also may contain an auxin and a cytokinin. The auxin may be indole-3-acetic acid, whereas the cytokinin may be 6-benzylaminopurine.

DETAILED DESCRIPTION

Definitions

In order to provide a clear and consistent understanding of the specification and the claims, including the scope given to such terms, the following definitions are provided.

"Apical dominance inhibitor" refers to noncytokinin compounds capable of promoting lateral bud break or adventitious meristem production. Apical dominance inhibitors include, but are not limited to, dikegulac (2,3:4,6-di-o-isopropylidene-2-keto-L-gulonic add), methyl laurate, and octadecyl-polyethoxyethanol (OPE).

"Callus" refers to a relatively undifferentiated proliferating mass of cells or tissue in vitro.

"Coding sequence" and "open reading frame" refer to a region of continuous sequential nucleic acid triplets encoding a protein, polypeptide, or peptide sequence.

"Dicot" or "dicotyledon" refers to plants that produce an embryo with two cotyledons. Examples of dicots include cotton, soybean, orange, grape, peanut, and other members of the Dicotyledonae.

"Embryogenic callus" refers to a type a callus capable of differentiating into somatic embryos.

"Endogenous" refers to materials originating from within the organism, cell, tissue or organ.

"Exogenous" refers to materials originating from outside of the organism, cell, tissue or organ. This typically applies to nucleic acid molecules used in producing transformed or transgenic host cells and plants.

"Monocot" refers to plants having a single cotyledon (the first leaf of the embryo of seed plants). Examples of monocots include cereals such as maize, rice, wheat, oats, barley, and other members of the Liliopsida.

"Non-embryogenic callus" refers to a type of callus composed of relatively undifferentiated, often highly vacuolated, cells that have not yet undergone embryogenesis.

"Nucleic acid" refers to deoxyribonucleic acid (DNA) and ribonucleic acid (RNA).

"Phenotype" refers to traits exhibited by an organism resulting from the interaction of genotype and environment.

"Polyadenylation signal" or "polyA signal" refers to a nucleic acid sequence located 3' to a coding region that promotes the addition of adenylate nucleotides to the 3' end of the mRNA transcribed from the coding region.

"Promoter" or "promoter region" refers to a nucleic acid sequence, usually found upstream (5') to a coding sequence, that controls expression of the coding sequence by controlling production of messenger RNA (mRNA) by providing the recognition site for RNA polymerase or other factors necessary for start of transcription at the correct site.

"Recombinant nucleic acid vector" refers to any agent such as a plasmid, cosmid, virus, autonomously replicating sequence, phage, or linear or circular single-stranded or double-stranded DNA or RNA nucleotide segment, derived from any source, capable of genomic integration or autonomous replication, comprising a nucleic add molecule in which one or more nucleic add sequences have been linked in a functionally operative manner. Such recombinant nucleic acid constructs or vectors are capable of introducing a 5' regulatory sequence or promoter region and a DNA sequence for a selected gene product into a cell in such a manner that the DNA sequence is transcribed into a functional mRNA, which is subsequently translated into a polypeptide or protein. Recombinant nucleic add constructs or recombinant vectors may be constructed to be capable of expressing antisense RNAs, in order to inhibit translation of a specific RNA of interest.

"Regeneration" refers to the process of growing a plant from a plant cell (e.g., plant protoplast, cell, tissue, or explant).

"Selectable marker" refers to a nucleic acid sequence whose expression confers a phenotype facilitating identification of cells containing and expressing the nucleic add sequence. Selectable markers include those that confer resistance to toxic chemicals (e.g., ampicillin resistance, kanamycin resistance, glyphosate resistance), complement a nutritional deficiency (e.g., uracil, histidine, leucine), or confer a selective physiological advantage (e.g., phytohormone or unique carbon source metabolism), or impart a visually distinguishing characteristic (e.g., color changes, enzymatic assay, or fluorescence).

"Transcription" refers to the process of producing an RNA copy from a DNA template.

"Transformation" refers to a process of introducing an exogenous nucleic acid sequence (e.g., a vector, recombinant nucleic acid molecule) into an organelle, cell, tissue, organ, or protoplast in which that exogenous nucleic acid is incorporated into a chromosome or is capable of autonomous replication.

"Transgenic" refers to organisms into which exogenous nucleic add sequences are integrated.

"Vector" refers to a plasmid, cosmid, bacteriophage, virus, transposon, or stretch of DNA that contains exogenous DNA to be transferred into a host organism.

"Zygotic embryo explant" refers to tissue(s) obtained from the zygotic embryo to be introduced into tissue culture.

The present invention discloses improved methods for the preparation of transgenic plants. It has particular utility with dicot species, especially those that have proven recalcitrant to previous transformation/regeneration protocols. The preferred embodiment utilizes the disclosed methods to generate transgenic cotton or soybean plants. The improvements are accomplished through the utilization of apical dominance inhibitors, which facilitate the formation of multiple shoots and thus increase the regenerability in recalcitrant genotypes.

To initiate a transformation process in accordance with the present invention, it is first necessary to construct a recombinant nucleic acid vector. This molecule is defined above and typically comprises a promoter, a coding sequence or other nucleic acid sequence of interest (e.g., having agronomic utility), a polyadenylation signal, a 3"-termination sequence, and a coding sequence for a selectable marker. It is understood to those skilled in the art that other regulatory elements may be needed or desired in the vector to obtain a particular result and such modifications are considered herein.

Means for preparing recombinant vectors are well known in the art. The present invention utilizes recombinant nucleic acid vectors that are generally functional in cotton and other plant species. A number of promoters that function in plant cells have been described in the literature and are derived from a variety of sources. These plant-specific promoters include the nopaline synthase (NOS) and octopine synthase (OCS) promoters, carried on tumor-inducing plasmids of *Agrobacterium tumefaciens*; the caulimovirus promoters, such as the cauliflower mosaic virus (CaMV) 19S and 35S promoters and the figwort mosaic virus (FMV) 35S promoter; the enhanced CaMV35S promoter (e35S); the light-inducible promoter from the small subunit of ribulose bisphosphate carboxylase (ssRUBISCO, a very abundant plant polypeptide); and promoters from actin and the chlorophyll a/b binding proteins. All of these promoters have been used to create various types of DNA constructs that have functioned successfully in plants (PCT publication WO 84/02913).

Modified promoters can be constructed to provide or alter particular regulatory features. Such activities include enhanced transcriptional activity (U.S. Pat. No. 5,106,739), inducibility, tissue-specificity, and developmental stage-specificity. In plants, promoters that are inducible, of viral or synthetic origin, constitutively active, and temporally regulated and spatially regulated have been described (see, for example, Odell et al.,—Nature 313: 810-812, 1985). Other promoters that function in a similar manner are also known in the art and have utility in the practice of this invention.

The promoters described may be further modified to further affect various regulatory features. Such promoters can be produced through combination with other regulatory elements (e.g., operators and enhancers), random mutation, or site-directed mutagenesis. For example, a promoter may be altered to contain multiple enhancer sequences to assist in elevating gene expression.

The recombinant nucleic acid vector typically comprises the regulatory elements sufficient for transcription of a mRNA. These elements include a 5' promoter sequence, a 5' non-translated sequence, a poly-A signal, and a 3' termination signal. These elements may be derived from a variety of sources. The DNA sequences may be isolated for use from viruses, other eukaryotic cells, or be of synthetic origin. In addition to the regulatory elements, the recombinant vector may also contain a selectable marker. The nucleic acid sequence serving as the selectable marker functions to produce a phenotype in cells that facilitates their identification relative to cells not containing the marker. Useful selectable markers include β-glucuronidase (GUS), green fluorescent protein (GFP), luciferase (LUX), antibiotic resistance sequences, herbicide tolerance sequences, and sequences such as phosphomannose isomerase that converts a carbon source that does not support growth into a growth carbon source.

Characteristics of useful selectable markers for plants have been outlined in a report on the use of microorganisms (Advisory Committee on Novel Foods and Processes, July 1994). These characteristics include stringent selection with minimal contaminating nontransformed tissue, high numbers of independent transformation events without interference in subsequent regenerative steps, application to a large number of species, and availability of an assay to detect the marker. Several antibiotic and herbicide resistance markers satisfy these criteria (Dekeyser et al., Plant Physiol., 90:217-223, 1989; Della-Cioppa et al., Bio/Technology, 5:579-584, 1987). Antibiotic resistance to kanamycin (and neomycin, G418, bleomycin) is provided by nptII, hygromycin B by aph IV, and gentamycin by aac3 or aacC4. Resistance to herbicides like glyphosate is also described.

In addition to the other components, the recombinant nucleic acid vector contains a DNA coding sequence of interest. These sequences may comprise any sequence of nucleic acids but are preferably those that code for proteins, polypeptides, or peptides conferring a desired trait, or phenotype. Examples of such traits include pest tolerance, herbicide tolerance, improvements in yield, nutritional enhancement, environmental or stress tolerance, or any other desirable changes in plant growth, development, and morphology.

In cotton, the coding sequence of a *Bacillus thuringiensis* (B.t.) crystal toxin has been successfully used to provide resistance to lepidopteran and coleopteran insects. Cotton has been successfully transformed with a B.t. gene, thereby rendering the plant tolerant to the effects of these pests. Others have used a glyphosate-tolerance coding sequence to rendering the cotton plants tolerant to glyphosate herbicides (Nida et al., J.—Agric. Food Chem., 44:1960-1966, 1996). Thus there are a variety of possible traits that may have agronomic significance. Any of these DNA coding sequences may be useful in the practice of the transformation methods disclosed herein.

Alternatively, the DNA coding sequence may be placed in a reverse orientation in the recombinant nucleic acid vector so as to produce an antisense RNA molecule. This molecule may be capable of hybridizing with a complimentary sequence in the cell. By hybridizing in this fashion, the antisense RNA molecule may completely or partially inhibit the translation of the complementary sequence (Schuch et al., Symp. Soc. Exp. Biol. 45:117-127, 1991; Bird et al., Biotech Gen. Engin. Rev., 9:207-227, 1991).

The RNA produced from the DNA coding sequence may also be a catalytic RNA molecule (e.g., a ribozyme). This class of RNA is designed to cleave another specific endogenous mRNA, which may effectively neutralize the normal function of the target RNA (see, for example, Gibson, Mol. Biotechnol. 7:125-137, 1997).

Not only may the DNA coding sequences have a variety of biological functions, as described above, they may also originate from diverse sources. The sequences may be derived from the same species of plant, a different species of plant, or a different organism. In addition, the sequence may comprise a synthetic nucleic add or a naturally occurring sequence that has been manipulated using molecular biological techniques.

In light of this disclosure, there exist numerous sequences from diverse sources with a large variety of functions. The foregoing discussion is provided by way of example and is not intended to be exhaustive. Any sequence of nucleic acid, regardless of source or function may have utility in the present invention.

After the construction of the plant transformation vector or construct, the recombinant nucleic acid vector may be introduced into a suitable host such as *Escherichia coli* and mated into another suitable host such as *Agrobacterium*, or alternatively, directly transformed into competent *Agrobacteria*. These techniques are well known to those of skill in the art and have been described for a number of plant systems, including cotton (U.S. Pat. Nos. 5,004,863 and 5,159,135).

*Agrobacterium*-mediated transfer is a widely applicable system for transforming plants because the DNA sequence can be introduced into whole plant tissues, thereby bypassing the need for using protoplasts to regenerate an intact plant. The use of—*Agrobacterium* to introduce DNA sequences into plant cells is well known in the art (Fraley et al., Proc. Natl. Acad. Sci. U.S.A., 80: 4803-4807, 1987; Rogers et al., Annu. Rev. Plant Physiol., 38:467-486, 1987). Furthermore, the integration of the T-DNA is a relatively precise process, resulting in few rearrangements. The DNA sequence being transferred is defined by border sequences that enable the intervening DNA sequence to be inserted into the plant genome.

*Agrobacterium* transformation vectors are capable of replication in—*Escherichia coli* as well as *Agrobacterium*, thereby allowing for convenient manipulations (Klee et al., Bio/Technology, 3:637-642, 1985). Moreover, recent technological advances in the structure of the vectors have simplified the process of inserting a specific DNA coding sequence into the vector in a suitable orientation. The structural improvements of these vectors comprise a convenient multi-cloning region containing multiple restriction sites, a flanking 5' promoter region, and a 3' polyadenylation site. The gene of interest is ligated into the multi-cloning site and is thus operably linked to the necessary 3' and 5' regulatory elements (Rogers et al., Methods Enzymol., 153:253-277, 1987). In addition,—*Agrobacterium* containing both armed and disarmed Ti genes can be used.

There are many variations of these types of vectors, and any that contain the necessary elements for producing mRNA from an inserted DNA coding sequence in a plant cell are suitable for participation in the invention. In those plant strains where—*Agrobacterium*-mediated transformation is efficient, the use of *Agrobacterium* is preferred due to the facile and defined nature of the gene transfer.

The present invention encompasses the use of bacterial strains to introduce genes into cotton plants. In the preferred embodiment, *Agrobacterium tumefaciens* is utilized for the transformation. Preferred *A. tumefaciens* strains include nopaline strains such as C58; octopine strains like LBA4404; and agropine strains such as EHA105, EHA101, and EHA109.

Transformation may also be accomplished via particle bombardment. PCT publication WO92/15675 describes the transformation of cotton by accelerating particles coated with DNA into the cells.

Technology for introduction of DNA into cells is well-known to those of skill in the art. Four general methods for delivering a gene into cells have been described: (1) chemical methods (Graham and Van der Eb, Virology, 54(2): 536-539, 1973.; Zatloukal et al., Ann. N.Y. Acad. Sci., 660: 136-153, 1992); (2) physical methods such as microinjection (Capecchi, Cell, 22(2): 479488, 1980), electroporation (Wong and Neumann, Biochim. Biophys. Res. Commun., 107(2): 584-587, 1982; Fromm et al., Proc. Natl. Acad. Sci. USA, 82(17): 5824-5828, 1985; U.S. Pat. No. 5,384,253), and the gene gun (Johnston and Tang, Methods Cell Biol., 43(A): 353-365, 1994; Fynan et al., Proc. Natl. Acad. Sci. USA, 90(24): 11478-11482, 1993); (3) viral vectors (Clapp, Clin. Perinatol., 20(1): 155-168, 1993; Lu et al., J. Exp. Med., 178(6): 2089-2096, 1993; Eglitis and Anderson,—Biotechniques, 6(7): 608-614, 1988); and (4) receptor-mediated mechanisms (Curiel et al., Hum. Gen. Ther., 3(2):147-154, 1992; Wagner et al., Proc. Natl. Acad. Sci. USA, 89(13): 6099-6103, 1992).

Methods for transformation of plant cells also include introducing DNA by—Agrobacterium-mediated DNA transfer (Fraley et al., Proc. Natl. Acad. Sci. U.S.A., 80: 4803, 1983), by direct DNA transfer into pollen (Zhou et al., Meth. Enzymol., 101: 433, 1983; Hess, Intern Rev. Cytol., 107: 367, 1987; Luo and Wu, Plant Mol. Biol. Reporter, 6: 165, 1988), by injection of the DNA into reproductive organs of a plant (Pena et al., Nature, 325: 274, 1987), by direct injection of DNA into the cells of immature embryos followed by the rehydration of desiccated embryos (Neuhaus et al., Theor. Appl. Genet., 75: 30, 1987), by protoplast transformation, by gene transfer into pollen, by injection into reproductive organs, by particle bombardment, by direct delivery of DNA such as by PEG-mediated transformation of protoplasts (Omirulleh et al., Plant Mol. Biol., 21: 415-428, 1993), by desiccation/inhibition-mediated DNA uptake, by electroporation, by agitation with silicon carbide fibers, by acceleration of DNA coated particles, etc. In some embodiments it may also be desirable to specifically transform plastids, such as chloroplasts or amyloplasts, by plastid transformation technology available in the art.

Each of these methods has distinct advantages and disadvantages. Thus, one particular method of introducing genes into a particular plant species, cultivar or genotype may not necessarily be the most effective for another plant species, but it is well known which methods are useful for a particular plant species, cultivar or genotype.

The transformation is typically performed on a specific type of plant tissue. The present invention is compatible with any regenerable tissues (i.e., tissue capable of forming a differentiated plant). Such tissue includes callus tissue, zygotic embryos, hypocotyl tissue, cotyledons, roots, floral tissue, petioles, anthers, and leaves. In the practice of the present invention, the regenerable tissue is preferably explants that contain shoot meristem tissue or primordia.

Preparation of Agrobacteria for inoculation of explants is generally well known to those of skill in the art. For purposes of the present invention, the Agrobacterium culture is initiated by inoculating a petri plate containing media such as Luria-Burtani (LB) in agar with selective antibiotics. The concentrations of selective agent as well as the particular selective agent utilized is variable and depends on the host strain. Those of skill in the art are also aware that the timing of culture growth, culture temperature, and concentration of host bacterium may be different for particular transformation systems. The inoculated plate is incubated between about 23° C. and about 30° C., and preferably between about 26° C. and about 28° C. for several days. An individually isolated colony is used to inoculate a LB, YEP, AB, etc. liquid culture +/−strain- and plasmid-selective antibiotics and grown to the proper concentration. The fresh liquid culture is subsequently used for inoculation of the explants.

Preparation of zygotic embryo explant tissue for in vitro culture from mature, dry seeds, especially field-grown cotton seeds is known to be a difficult process requiring much experimentation to achieve repeatable success. Briefly, cotton seeds are sterilized and imbibed overnight in a cotton sterilization medium (carbenicillin (200 mg/L), cefotaxime (250 mg/L) and 6 mL of fungicide stock (1 g benlate, 1 g captan, and 1 g daconil in 100 mL of sterile distilled water) in 2 L sterile distilled water). The zygotic embryo axes are removed by hand and selected for the presence of intact apical domes. Soybean seeds are germinated overnight in BGM media, and the embryonic axes are removed as described below in Example 6.

Bean Germination Media (BGM) is prepared with BT Stock#1 (10 mL/L), BT Stock #2 (10 mL/L), BT Stock #3 (3 mL/L), BT Stock #4 (3 mL/L), ST Stock #5 (1 mL/L), sucrose (25 g/L), adjust to pH 5.8 and autoclave. Add prior to use 2.5 mL/L of cefotaxime (50 mg/mL) and 3 mL of fungicide stock (1 g chlorothalonile (75% WP), 1 g captan (50% WP), and 1 g benomyl (50% WP) in 100 mL of sterile distilled water). BT Stocks are prepared as described. Make and store each stock individually. Dissolve each chemical thoroughly in the order listed before adding the next. Adjust volume of each stock accordingly. Store at 4° C. BT Stock #1 contains $KNO_3$ (50.5 g/L), $NH_4NO_3$ (24.0 g/L), $MgSO_4*7H_2O$ (49.3 g/L), and $KH_2PO_4$ (2.7 g/L). BT Stock #2 contains $CaCl_2*2H_2O$ (17.6 g/L). BT Stock #3 contains $H_3BO_3$ (0.62 g/L), $MnSO_4.H_2O$ (1.69 g/L), $ZnSO_4-7H_2O$ (0.86 g/L), KI (0.083 g/L), $NaMoO_4.2H_2O$ (0.072 g/L), $CuSO_4-5H_2O$ (0.25 mL of 1.0 mg/mL stock per liter), and $CoCl_4-6H_2O$ (0.25 mL of 1.0 mg/mL stock per liter). BT Stock #4 contains $Na_2EDTA$ (1.116 g/L) and $FeSO_4 7H_2O$ (0.834 g/L). BT Stock #5 contains Thiamine-HCl (0.67 g/500 mL), Nicotinic Add (0.25 g/500 mL) and Pyridoxine-HCl (0.41 g/500 mL) and should be stored in a foil wrapped container.

Explants can be inoculated with Agrobacterium harboring a recombinant nucleic acid vector. The co-culture is allowed to proceed from one to five or more days, preferably three to five days at moderate temperature (i.e., about 22° C.-24° C.). After the co-culture step, the excess Agrobacteria are removed. Transformation efficiency can be increased in Agrobacterium transformation by wounding the explant prior to, during, or after inoculation with the Agrobacterium. Wounding methods may include, but are not limited to, vacuum infiltration, scalpel, needles, sonication, magnet-assisted, and desiccation.

Magnet-assisted wounding involves using magnetic metal particles and a magnet to produce microwounds in the tissue. It can be used for a variety of tissues (callus, embryos, or shoot tips). The tissue should be placed in a stiff medium to firmly hold the explants in a vertical position. The medium should also be thinly poured so that the tissue is close to the bottom of the petri dish. Suitable magnetic particles must be used. Many magnetic particles are toxic to the cells. Preferably carbonyl iron particles in the 1-10 μm size are used, but any non-toxic magnetic particle could be used. The particles are added to the—Agrobacterium solution and mixed gently. The suspension can then be added to the tissue either in the presence or absence of the magnet. Suitable magnets have wide poles and are approximately the same diameter as the 100×25 mm petri plate and have a very high field density per area. The preferred device is a permanent magnet of neodymium-iron-boron (2×2×1 inch block). Once the suspension is in the petri dish, the petri dish is moved over the surface of the magnet in a circular orbit at approximately 3 revolutions per second for 2 minutes. The orbit should let the target tissue revolve around the center axis of the field and not move over the edge of the magnet pole. At the end of the wounding, remove from the magnetic field and remove the tissue to a suitable co-culture medium. It is possible that the tissue could be wounded with a suspension of magnetic particles and the Agrobacterium added subsequently for inoculation and co-culture.

The tissue is subsequently transferred to selective media containing one or more antibiotics or metallic compounds to prevent further growth of the Agrobacterium. The range of inhibitory antibiotics may vary, depending on the Agrobacte-

*rium* strain used. Those of skill in the art are familiar with the antibiotics and metallic compounds used to inhibit *Agrobacterium* remaining in the culture while allowing growth of the transgenic explant tissue. Examples of *Agrobacterium* inhibitory antibiotics useful for practice of this invention include carbenicillin and cefotaxime. Examples of microbial-inhibiting metals include silver, copper, zinc, iron, and mercury.

In addition to antibiotics to inhibit the growth of *Agrobacteria*, a selection agent may be added to promote the growth of the transformed plant tissue. The selection agent is a substance that is inhibitory or neutral to non-transformed cotton cells and neutral or stimulatory, respectively to transformed cells. The transformed cells generally incorporate and utilize the selectable marker at a level suitable to confer a selective advantage to the transgenic cell, tissue, organ, or plant. Selection agents used may generally be any positive- or negative-acting agent compatible with the present invention. The selection agent is preferably kanamycin, at a concentration between about 15 mg/L and 1500 mg/L, or glyphosate, at a concentration between about 0.0025 mM and 2.5 mM. One skilled in the art will appreciate that the concentration of the selection agent may vary with the cultured cells, tissues or organs and media employed as well as the particular selection agent utilized.

Many different forms of culture media are suitable for the selection culture. One skilled in the art is familiar with the varieties of media that, when supplemented appropriately, support plant tissue growth and development. Examples of such media would include, but are not limited to, MS media (Murashige and Skoog, Physiol. Plant, 15: 473-497, 1962), Gamborg's media (Gamborg et al., Exp. Cell Res., 50:151, 1968), Woody Plant Media (WPM) (McCown and Lloyd, Hort. Science 16:453, 1981), Nitsch and Nitsch media (Nitsch and Nitsch, Science 163:85-87, 1969), Schenk and Hildebrandt media (Schenk and Hildebrandt, Can. J. Bot. 50:199-204, 1972), modified LP medium (VonArnold and Eriksson, Can. J. Bot. 59:870-874,1981; after Lepoivre and Quoirin, Acta Hortic. 78:437-2, 1977), DKW medium (Driver and Kuniyuki, HortScience 19(4): 507-509, 1984; and as modified by Neuman et al., Plant Cell, Tiss. Organ Cult. 32:9-18, 1993; and as available from Sigma Co., product: D6162), GD1 medium (Gresshoff and Doy, Planta 107: 161-170, 1972; and as used by Sommer et al., Bot. Gaz. 136(2): 196-200, 1975; and as modified), and MS/B5 medium (salts by Murashige and Skoog, Physiol. Plant. 15:473-485, 1962, with B5 vitamins from Gamborg et al., Exp. Cell Res. 50:151-158, 1968. And as formulated by either: Sigma Co., product M0404; Gibco Co., product 500-1117EH plus Sigma G-2519; or Phytotechnology Labs, product M524 plus G219). Any of these culture media, as well as any equivalent forms, fall within the scope of the present invention. In an embodiment, the culture media for cotton is MS/B5 or GD1 media, wherein the MS media typically contains additives. The preferred media for soybean is WPM. The additives generally comprise vitamins such as $B_5$ vitamins, phytohormones such as auxins and cytokinins, and a carbohydrate source such as glucose. The media may or may not be gelled.

Auxins such as indolebutyric acid (IBA), napthalene acetic acid (NAA), 2,4-dichlorophenoxyacetic acid (2,4-D), 4-chlorophenoxyacetic acid (4-CPA), 2,4,5-trichlorophenoxypropionic acid (2,4,5-TP), dicamba, or picloram can be used. Preferably indole acetic acid (IAA) is used. Cytokinins such as kinetin, zeatin, thidiazuron (TDZ) or $N^6\Delta^2$-isopentenyl adenine (21P) can be used. Preferably benzylaminopurine (BAP) or zeatin riboside (ZR) is used.

The selection media also contains an apical dominance inhibitor, such as dikegulac, methyl laurate, or OPE. What is desired are compounds that reduce the internal factors within the plant tissue that provide apical dominance and/or interfere with cytokinin's ability to make shoots. Inhibiting auxin production appears to be much more important than merely blocking its movement. So-called "anti-auxins" (such as TIBA [2,3,5-triiodobenzoic acid], 4CPA [o-chlorophenoxyacetic acid], and NPA [1-N-naphthylphthalamic acid)) are actually auxin transport inhibitors and have little effect in cotton. Cytokinins are also anti-auxins, but exogenous cytokinins often kill cotton tissues. Thus a chemical such as dikegulac allows recalcitrant tissues to respond in tissue culture to its own hormones or exogenously applied growth factors. The desired concentration of dikegulac varies from system to system and usually is between about 5 to 5000 mg/L, and can be between about 10 to 1000 mg/L.

The plants are usually subjected to multiple rounds of selection and multiple shooting. Each round in fresh media produces more shoots, and selection insures that only transformed shoots survive. After enough rounds, the shoots that remain should not be chimeric and then can be rooted to give germline transformed plants.

Those of skill in the art are aware of other important variables that may be altered in the tissue culture conditions. Temperature is one such variable. The transformation and regeneration processes are generally performed in a temperature range between about 20° C. and about 30° C. Usual temperature ranges for multiple bud and shoot production are from about 25-28° C. depending on other physical conditions. Another variable is the amount of light provided to the cultures. Plant tissue is typically cultured in vitro with a 16-hour light and 8-hour dark photoperiod with light intensities between about 10 μE and about 350 μE, unless other conditions are specified. Light intensities for in vitro cotton shoots can be from about 10-50 μE PAR.

The transformed tissue is exposed to selection conditions for about four to ten weeks, usually about four to eight weeks. Transfers are performed as needed, generally every three to eight weeks.

As a result of the transformation of apical meristems by any method, the plant tissue is only partially transformed and is chimeric with respect to transgenic and non-transgenic cells. The tissue is subsequently exposed to dikegulac or another apical dominance inhibitor to induce adventitious and lateral meristems, buds, and shoots to improve the chimeric transgenic sector size and quality. In this case, quality is defined as the stability of the transgenic sector in the growing point and new developing tissue, and its incorporation into the germline of the plant. The preferred embodiment of dikegulac exposure is the DIB medium described hereinafter. Tissues previously exposed to dikegulac, such as in DIB media, can be recultured on dikegulac-containing media, which initiates a second flush of buds and shoots. This multiplies the number of induced meristems, buds and shoots with each subsequent transfer and can be repeated as many times as desired.

The ability to multiply the meristems, buds, and shoots greatly enhances the chance of transformation success and also serves to enable the use of selection agents to improve the size and quality of the transgenic sectors. Without the production of adventitious or lateral shoot apical meristems, selection agents usually fail to enhance transgenic sectors in meristem transformations. This is particularly true in cotton. The ability to produce recurrent meristems, buds, and shoots enables the selection process by providing new dividing and growing points on which the selective agents can act. Some of these new points will contain larger and higher quality transgenic sectors and will accordingly respond favorably to the selective agent. In addition, new meristems that develop while under selection pressure are much more likely to contain a high percentage of cells with the transgene. Large, quality transgenic sectors in the shoot apical meristem are critical to production of transgenic germline cells, which are required for the event to be heritable.

An especially attractive explant for the transformation process includes these recurrent shoot cultures such as those developed on DIB media. Using recurrent shoot cultures as the explant for the transformation instead of the original apical meristem tissue provides a larger, multiple-meristematic and rapidly growing target for the transformation process. Thus, it may be useful to pre-expose the explant or recurrent tissues to dikegulac before the transformation process. In addition, when embryo explants are cultured on DIB medium prior to transformation, the shoot apical meristem alters its morphology, becoming a wholly new type of enlarged, spherical meristematic tissue that no longer resembles (histologically or visually) an apical or lateral meristem. Despite these changes, it is capable of adventitious as well as lateral meristem, bud and shoot development. This new tissue is also a particularly attractive target tissue for the transformation process.

EXAMPLES

The following examples further illustrate the present invention. They are in no way to be construed as a limitation in scope and meaning of the claims.

Example 1

Cotton zygotic embryo culture: Untreated delinted, dry cotton seeds were sterilized in freshly made 50% Chlorox plus 2 drops of Tween 20 per 2 liters. Seeds were sterilized for 9-10 minutes. Seeds were rinsed 3 times with sterile distilled water; on the second rinse, the seeds were allowed to soak for 5 minutes prior to removing the water. Seeds were aseptically transferred to sterile 1 liter beakers and equally distributed into 2 beakers. Approximately 600 mL of Cotton Sterilization Medium (CSM) was added to each beaker containing decontaminated seeds. CSM contains carbenicillin (200 mg/L), cefotaxime (250 mg/L) and 6 mL of fungicide stock (1 g benlate, 1 g captan, and 1 g daconil in 100 mL of sterile distilled water) in sterile distilled water.

Each beaker was covered with sterile aluminum foil and placed in the dark at room temperature for overnight imbibition. The next day, CSM was removed and seeds were transferred to sterile petri dishes, which were placed in a covered container and placed in a growth chamber at 15° C. in continuous dark. CSM is not added to the seeds at this point. Seeds can be used the same day or remain at 15° C. for 1-2 days.

Seeds were removed from dark growth chamber and placed in a laminar flow hood. Zygotic embryos were removed from the seed coat and cotyledons were detached from the cot-node of the embryo axis by popping the zygotic embryo axes into a sterile petri dish containing CSM by holding the seed between the thumb and index finger and squeezing the lower quarter of the seed near the radicle. This method frees the embryos of the cotyledons. Embryo axes were washed twice with fresh CSM or water. Fresh CSM or sterile water containing antibiotics was added to the petri dish containing embryos and, the embryos were transferred to the 15° C. percival for an overnight incubation. This overnight incubation is important to eliminate microbial field contaminants. Embryos can be used the next day for experimental setup.

Using a dissecting microscope, embryos that have intact apical domes and preferably intact radicles were selected. Embryos that have split hypocotyls, no apical domes, or are otherwise visibly damaged should be discarded. Embryos containing portions of the cotyledons can still be used but the cotyledon tissue needs to be carefully removed.

Example 2

Bacterial preparation: *Agrobacterium* cultures were prepared as known in the art (Maniatis et al. 1982. Molecular Cloning: A Laboratory Manual, Cold Spring Harbor Press). Specifically, disarmed *Agrobacteria* containing binary vector(s) are streaked from freezer onto LBSCK plates (contains LB medium plus 1.0 mL of spectinomycin, 0.5 mL of chloramphenicol, 0.5 mL of kanamycin per 500 mL of medium). (Spectinomydn stock=100 mg/mL; chloramphenicol stock=25 mg/mL; kanamycin stock=50 mg/mL.) Bacteria can be incubated at room temperature or in an incubator at 27° C.; bacterial colonies should be seen within 24 days. Bacterial should be streaked from freezer every 34 weeks. Streak a fresh plate from the freeze plate 2-3 days prior to experimental setup. One to two days prior to the inoculation of the explants, transfer 1 colony of bacteria from a freshly streaked plate to a culture tube containing 5 mL of YEP medium. YEP medium contains the following: log/L peptone, log/L yeast extract, 5 g/L NaCl. The following antibiotics are added after autoclaving: 1.0 mL of spectinomycin, 0.5 mL of chloramphenicol, 0.5 mL of kanamycin per 500 mL of medium. Place the tube of bacteria on a rotary tumbler or orbital shaker at suitable speed at ~26° C. The afternoon prior to inoculating the explants, add 4-6 mL of the bacterial culture to 50 mL of ABSCK medium in sterile flasks. Shake or rotate the flasks overnight at a speed sufficient for proper aeration. Transfer the overnight bacterial cultures to a centrifuge tube and spin the bacteria for 10-15 minutes at 2000 rpms at room temperature. A pellet should form at the bottom of the tube and the supernatant should be somewhat cloudy (under normal conditions, 30 mL of bacterial culture is pipetted into a 50 mL conical tube). To take OD readings, the spectrophotometer should be set at 660 nm; the bacterial cultures should be diluted 1:10 prior to taking an absorbence reading. Dilute the bacteria in the co-culture medium; this is normally a $\frac{1}{10}$ strength medium plus 200 µM acetosyringone, 1 mM galacturonic add, pH 5.5. The bacterial cultures should be shaken on an orbital shaker while the explants are prepared for infection.

Example 3

Transformation: Zygotic embryos from cotton cultivar DP50 were prepared as described in Example 1. Embryos were then not wounded, wounded with magnetic particles pulled within a magnetic field, wounded by vacuum infiltration, cut with a scalpel, poked with a needle, or desiccated.

Desiccation wounding is done by placing the embryos on a Whatman #1 filter paper in a petri dish. The dishes are then left in the flowing air of a horizontal sterile laminar air hood for 30 minutes to 1 hour. The embryos are then removed from the dry filter paper and placed directly into another petri dish containing an *Agrobacterium* suspension prepared as described in Example 2 for inoculation. After inoculating for 30 minutes, the embryos were co-cultured for 2-7 days.

Magnet-assisted wounding involves using magnetic metal particles and a magnet to produce microwounds in the tissue.

The embryos were placed on a stiff medium of Xanthan Gum to firmly hold the explants in a vertical position. Carbonyl iron particles (60-70 mg) in the 1-10 μm size were used (Gredman Ltd., Taiwan). The particles were added to 2 mL of the *Agrobacterium* solution and mixed gently. The suspension can be added to the tissue either in the presence or absence of the magnet. A permanent magnet of neodymium-iron-boron (2×2×1 inch block) was used. Once the suspension is in the petri dish, the petri dish is moved over the surface of the magnet in a circular orbit at approximately 3 revolutions per second for 2 minutes. The orbit should let the target tissue revolve around the center axis of the field and not move over the edge of the magnet pole. At the end of the wounding, remove from the magnetic field and remove tissue to a suitable co-culture medium.

Vacuum infiltration was performed by covering the explants with—*Agrobacterium* suspension. The mixture was then placed in a vacuum chamber and the house vacuum (~28 mmHg) was applied either steadily or pulsed up to 4 times for 1 hour. The explants were then co-cultured as described below.

For scalpel wounding, a #11 scalpel blade was used to make several small incisions in the apical region of the embryos. The embryos were then transfered to the—*Agrobacterium* suspension and inoculated for 30 minutes and then co-cultured as described below.

For needle wounding, shader tattoo needles were used to wound the apical meristem and surrounding region. The embryos were inoculated for 30 minutes and then co-cultured.

Figure 1:
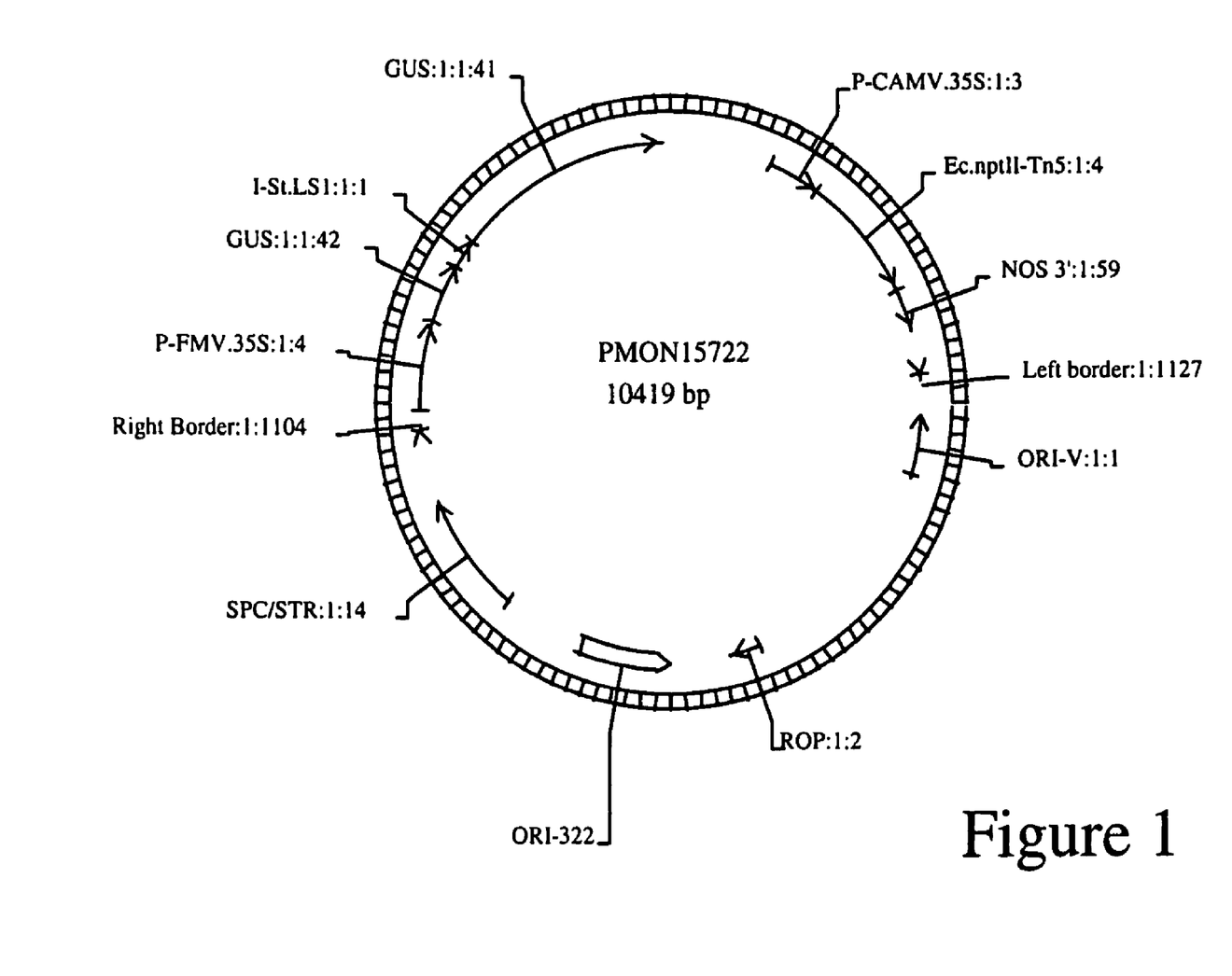
FIG. 1 is a plasmid map of pMON15722.

After wounding and inoculation, the embryos were co-cultured with the—*Agrobacterium* containing a GUS gene with a promoter (pMON15722; FIG. 1) under the following conditions. The co-culture period was on the Xanthan Gum medium with mannitol+sorbitol in petri dishes (of various sizes), for 3 to 5 days at cool conditions (~22-28° C.). Following co-culture, the explants were transferred to GD1 medium with 400 mg/L Dikegulac-free acid+1 mg/L IAA+1 mg/L BAP+50 mg/L kanamycin. Explants were only allowed to grow in this for 1 day and then were sacrificed for GUS expression. Results are shown in Table 1.

TABLE 1

Wounding Parameters

| Experiment | Treatment | # Explants | GUS expression (%) in hypocotyl | GUS expression (%) in regeneration zone |
|---|---|---|---|---|
| 1 | no wounding | 41 | 4 (9.8) | 2 (4.9) |
|   | magnet | 88 | 18 (20.5) | 6 (6.8) |
|   | vacuum infilt. | 95 | 16 (5.9) | 1 (1.0) |
|   | scalpel | 48 | 10 (20.8) | 5 (10.4) |
|   | needles | 36 | 3 (8.3) | 0 (0.0) |
| 2 | magnet | 32 | 7 (21.9) | 3 (9.4) |
|   | vacuum infilt. | 30 | 4 (13.3) | 1 (3.3) |
|   | desiccation | 40 | 14 (35.0) | 13 (32.5) |
| 3 | desiccation | 82 | 39 (47.6) | 23 (28.0) |
|   | desiccation post inoculat. | 74 | 37 (50.0) | 11 (14.9) |
|   | desiccation pre and post inoculation | 132 | 26 (19.7) | 29 (22.0) |

Example 4

Tissue culture: Embryo explants are cultured in media in a suitable culture vessel containing 500 mg/L sodium dikegulac (2,3:4,6-diisopropylidene-2-keto-1-gulonic acid), 1 mg/L IAA (indole-3-acetic acid), and 1 mg/L BA (N-6-benzyladenine) (herein after referred to as DIB media). Any common plant tissue culture media can be used, including, but not limited to, modified LP medium, DKW medium, GD1 medium, MS/B5 medium, or WPM medium. Embryo axes should be placed apical end up and basal end into the medium so that the radicle is beneath the medium surface. The explants are cultured axenically at approximately 25-28° C. under fluorescent lighting at about 10-50 μE PAR for a 16-hour photoperiod. Typically it takes 5-10 weeks for multiple shoots in cotton to develop to a useful size.

Elongation and rooting After multiple shoots are produced, individual shoots, epicotyls, or entire shoot clump developed on the explant are excised and subcultured on the basal medium used above (without the growth regulators, or with exogenous auxin) under the same temperature and light conditions.

Example 5

Forms of dikegulac: Dikegulac comes in several forms, for example a sodium salt, Atrimmec™, and free add. Early experiments were done using 1000 mg/L of the sodium salt incorporated into the culture medium for cotton. This concentration produced swelling, enlarged meristems, and adventitious-like leaf primordia, but the explants did not easily grow out. Later tests reduced this to 500 mg/L for ease of shoot development. Sodium dikegulac (500 mg/L) was tested in all combinations with BAP (0, 1, and 5 mg/L) and IAA (0, 1, and 5 mg/L). For US upland cotton varieties, 500 mg/L dikegulac, 1 mg/L IAA and 1 mg/L BA is a particularly useful combination. Zeatin riboside (ZR) can be substituted for BA with good results. The cytokinin component can also be omitted with good results.

Use of DI (Dikegulac+IAA), or DIB (Dikegulac+IAA+BA) media allows in vitro production of multiple, axillary, and adventitious buds and shoots in elite cotton varieties (Table 2).

TABLE 2

Response of selected elite germplasm to DIB medium treatments.

| Cultivars Tested | % Multiple Shoot Response | Subjective Vigor rating |
|---|---|---|
| SG 747 | 68% | medium |
| SG 125 | 85% | medium |
| SH 26 | 41% | low |
| PM 2379 | 73% | high |
| DP 388 | 41% | medium |
| DP 50 | 80+ | high |

Zygotic embryo explants were cultured on DIB-containing media and under standard conditions listed herein.

Experiments were done to determine if the form of the dikegulac is important and to determine a minimum optimum level of dikegulac needed for multiple shoot formation. Table 3 shows these results along with a comparison of two different basal media (MS/B5 and GD1). What is not captured in the numerical data in Table 3 is the overall phenotypic response of the cultures. The explants cultured on the MS/B5 medium contained a lot of callus tissue at the base and the cultures were yellowing. The cultures on GD1 contained only a minimal amount of callus but the yellowing of the regenerating tissues was present.

TABLE 3

Multiple shoot formation from cotton embryos cultured on varying levels of dikegulac (acid form) with 1 mg/L IAA and 1 mg/L BAP.

| Medium | Dikegulac conc (mg/L) | # Responding | Type of response |
|---|---|---|---|
| MS/B5 | 100 | 36/50 | single shoots |
| GD1 | 100 | 39/50 | single shoots |
| MS/B5 | 200 | 9/50 | single shoots |
|  |  | 38/50 | multiple shoots |
| GD1 | 200 | 22/50 | single shoots |
|  |  | 21/50 | multiple shoots |
| MS/B5 | 300 | 3/50 | single shoots |
|  |  | 41/50 | multiple shoots |
| GD1 | 300 | 10/50 | single shoots |
|  |  | 33/50 | multiple shoots |
| MS/B5 | 400 | 40/50 | multiple shoots |
| GD1 | 400 | 37/50 | multiple shoots |
| MS/B5 | 500 | 38/50 | multiple shoots |
| GD1 | 500 | 40/50 | multiple shoots |
| MS/B5 | 500 (sodium salt) | 39/50 | multiple shoots |
| GD1 | 500 (sodium salt) | 35/50 | multiple shoots |

A commercial form of dikegulac called Atrimmec® (pbi/Gordon Corporation, Kansas City, Mo.) has been used in soybean.

Table 4 is a comparison of many different formulations of dikegulac. Elongated, rooted cotton shoots produced via either the sodium salt, or free acid form of dikegulac developed into morphologically normal cotton plants with 100% fertility.

TABLE 4

Relative activity of different formulations of dikegulac on DP50 cotton zygotic embryo explants.

| Dikegulac Formula[1] | No. Culture Vessels | Total No. Explants[3] | No. non-viable Explants[4] | Percent Responding | Extra buds per viable explant[5] |
|---|---|---|---|---|---|
| Study 1 |  |  |  |  |  |
| At 350, solid[2] | 6 | 60 | 16 | 73% | 2.5 |
| At 350, liq.[2] | 6 | 48 | 10 | 79% | 3.4 |
| At 700, solid | 6 | 60 | 31 | 48% | 3.8 |
| Q2161, solid | 6 | 60 | 9 | 85% | 2.9 |
| Q2161, liq. | 7 | 56 | 20 | 64% | 3.5 |
| D4043, solid | 6 | 60 | 5 | 92% | 3.4 |
| D4043, liq. | 7 | 56 | 16 | 84% | 3.9 |
| Free Ac., solid | 6 | 60 | 8 | 87% | 3.8 |
| Free Ac., liq. | 6 | 48 | 16 | 67% | 3.4 |
| RJK-H, solid | 6 | 60 | 9 | 85% | 3.7 |
| RJK-D, liq. | 6 | 60 | 11 | 82% | 3.3 |
| Study 2 |  |  |  |  |  |
| D4043, solid | 6 | 46 | 8 | 83% | 4.1 |
| Free Ac., solid | 5 | 27 | 1 | 96% | 4.2 |
| Control | 4 | 32 | 2 | 94% | 0.0 |
| Study 3 |  |  |  |  |  |
| RJK-H, 400 | 10 | 80 | 20 | 75% | 1.9 |
| RJK-H, 500 | 10 | 80 | 17 | 79% | 3.0 |
| RJK-H, 600 | 10 | 80 | 24 | 70% | 3.4 |
| RJK-H, 700 | 10 | 80 | 33 | 59% | 3.1 |

[1]At = Atrimmec (Gordon's Turf & Ornamental Products; values in mg/L sodium dikegulac equivalent); Q2161 = 500 mg/L dikegulac, sodium salt (Aldrich, Q2161-1); D4043 - 500 mg/L dikegulac, sodium salt (Sigma, D4043); Free Ac. = 500 mg/L dikegulac, free acid (Aldrich 17,969-8); RJK-H = 500 mg/L dikegulac, hydrated sodium salt (Gateway Chemical); RJK-D = 500 mg/L dikegulac, dry sodium salt (Gateway Chemical).
[2]Solid = gelled, semi-solid DIB medium; Liq. = liquid DIB medium.
[3]Explants are zygotic embryo explants excised from cottonseed cv DP50.
[4]Number of non-viable explants was determined by lack of embryo germination and shoot development in tissue culture.
[5]Number of clearly discernible shoot buds per viable explant - minus the native apical shoot.

Example 6

Use of Dikegulac to Produce Multiple Buds in Soybean (Particle Bombardment/Glyphosate Selection): Three elite soybean varieties were tested: A4922, A3469, and A3244. The original concentration curve tested 0, 10, 50, 100, 500 mg/L Atrimmec™ (dikegulac sodium). Fifty mg/L Atrimmec™ was found to be useful for soybean. Bud counts were taken at day 14-21 and day 42-56 for each of the three varieties. Transgenic shoots were also recovered at day 40-65.

Embryonic axes were excised from seeds germinated in liquid germination media (BGM) overnight at 20° C. in the dark. Primary leaf tissue was carefully removed to expose the meristematic region. Explants were plated on McCown's Woody Plant Media (WPM) plus 20 g/L sucrose, 1.3 g/L calcium gluconate, 60 mg/L benomyl, 200 mg/L carbenicillin and stored at 15° C. in the dark overnight.

DNA was prepared for the gene-gun blast by adding 100 µL of 0.1M spermidine to 20 mg of 0.82 µm gold beads. Four µL of 1 mg/mL DNA (200 ng DNA/mg gold final concentration) was added to the spermidine/gold and vortexed completely. During vortexing, 100 µL of 10% $CaCl_2$ was added dropwise. The DNA prep was allowed to precipitate for 10 minutes. The supernatant was removed and the DNA/gold precipitate was resuspended in 19 mL of 100% ethanol and 1 mL sterile distilled water (SDW). Blasting sheets were coated with 320 µL of bead prep. Beads were allowed to settle for approximately 30 seconds, ethanol was removed, and the sheets set aside to dry.

Figure 2:
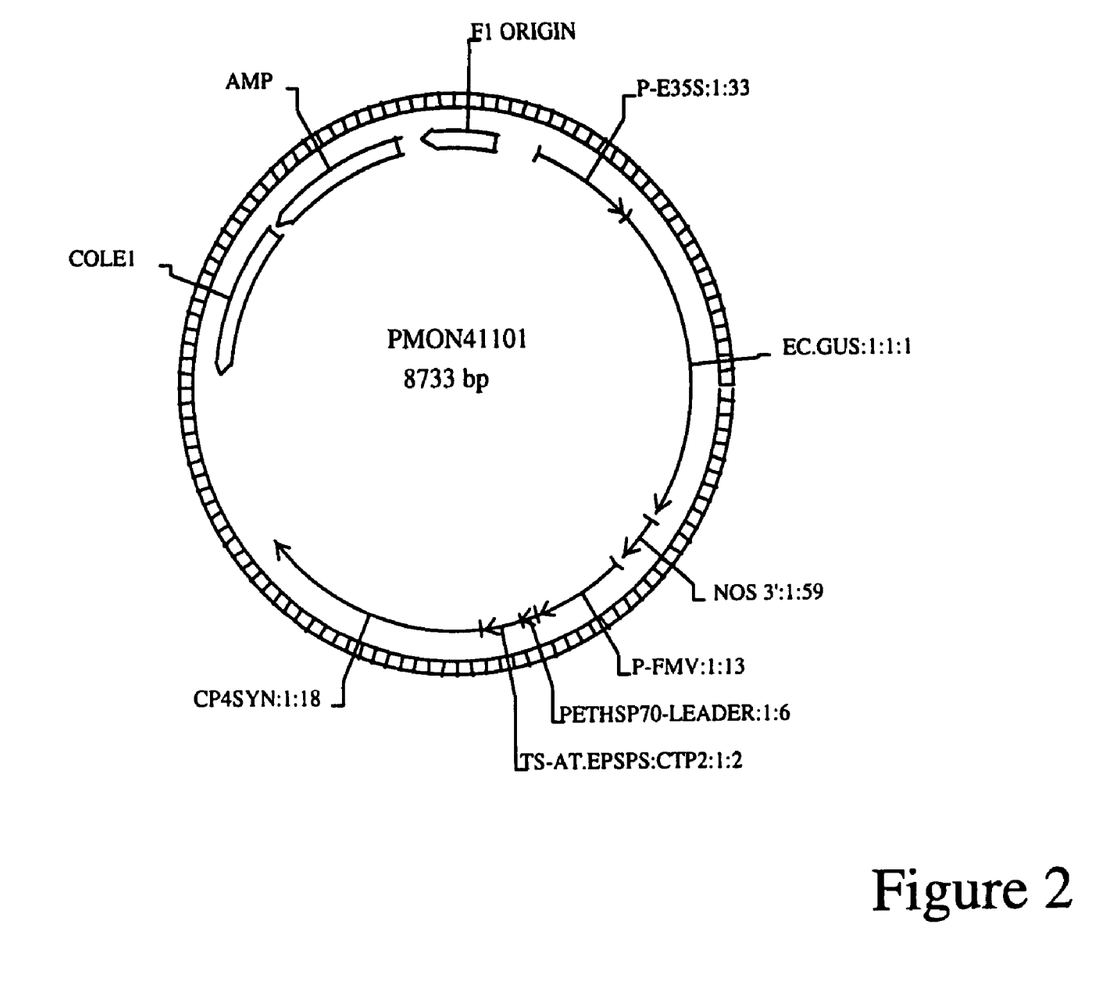
FIG. 2 is a plasmid map of pMON41101.

Explants were placed on target media (8% carboxymethylcellulose (low viscosity), 2% carboxymethylcellulose (medium viscosity), and 0.4% washed agar in distilled water) with meristems facing up. Targets were bombarded once using the electric gun with plasmid pMON41101 (FIG. 2). Explants were placed onto WPM media as described above with 75 µM glyphosate, plus either DIB (50 mg/L Atrimmec™ (dikegulac sodium)+1 mg/L IAA+1 mg/L BAP) or IB (hormone control) (1 mg/L IAA+1 mg/L BAP) or Hormone Free Control (media as listed above (i.e., no additions)).

Explants were placed in 28° C., 16-hour light/8-hour dark photoperiod. On day 14-21 all explants were transferred to the hormone free media. Results are presented in Table 5.

TABLE 5

| A4922 | | |
|---|---|---|
| Treatment | Avg # buds/explant at 4 wk | Avg # buds/explant at 6 wk |
| DIB (200 explants) | 6.7 | 8.0 |
| IB (100 explants) | 2.6 | 4.2 |
| Hormone-free (50 explants) | n/d | 3.3 |

| A3469 | | |
|---|---|---|
| Treatment | Avg #buds/explant at 2 wk | Avg #buds/explant at 7 wk |
| DIB (200 explants) | 4.2 | 6.5 |
| IB (100 explants) | 2.5 | 4.4 |
| Hormone-free (50 explants) | n/d | 4.1 |

| A3244 | | |
|---|---|---|
| Treatment | Avg # buds/explant at 3 wk | Avg # buds/explant at 8 wk |
| DIB (200 explants) | 3.7 | 6.1 |
| IB (100 explants) | 2.5 | 4.0 |
| Hormone-free (50 explants) | n/d | 3.1 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the invention has been described in detail for the purpose of illustration, it is understood that such detail is solely for that purpose, and variations can be made therein by those skilled in the art without departing from the spirit and scope of the invention which is defined by the following claims.

The invention claimed is:

1. A method for the regeneration of a plant comprising the steps of:
    a) providing regenerable tissue from soybean or cotton;
    b) culturing the regenerable tissue in a media comprising the apical dominance inhibitor dikegulac to produce shoots; and
    c) culturing the shoots to produce a plant,
    wherein the regenerable tissue is callus tissue, a zygotic embryo, hypocotyl tissue, cotyledon tissue, root tissue, floral tissue, petiole tissue, anther tissue or leaf tissue.

2. The method of claim 1, wherein said media also contains an auxin or a cytokinin.

3. The method of claim 2, wherein said media contains the auxin IAA.

4. The method of claim 2, wherein said media contains the cytokinin BA or ZR.

5. The method of claim 1, wherein the dikegulac is a salt.

6. The method of claim 1, wherein the dikegulac is a free acid.

7. The method of claim 1, wherein the dikegulac is present at a concentration from about 5 to about 5000 mg/L.

8. The method of claim 1, wherein the dikegulac is present at a concentration from about 10 to about 1000 mg/L.

9. The method of claim 1, wherein said plant is a cotton plant.

10. The method of claim 1, wherein said plant is a soybean plant.

11. The method of claim 1, wherein the media is MS, MS/B5, GD1, Gamborg's media, WPM, modified LP, DKW, Nitsch media, or Schenk and Hildebrandt media.

12. A method for the regeneration of a transgenic plant comprising the steps of:
    a) providing a regenerable tissue from soybean or cotton;
    b) introducing recombinant DNA into the tissue to generate a transformed tissue;
    c) culturing the tissue in a media comprising the apical dominance inhibitor dikegulac to produce transformed shoots; and
    d) culturing the transformed shoots to produce a transgenic plant,
    wherein the regenerable tissue is callus tissue, a zygotic embryo, hypocotyl tissue, cotyledon tissue, root tissue, floral tissue, petiole tissue, anther tissue or leaf tissue.

* * * * *